United States Patent [19]

Wood et al.

[11] Patent Number: 4,728,611

[45] Date of Patent: * Mar. 1, 1988

[54] PRODUCTION OF PHENYLALANINE WITH IMMOBILIZED CELLS

[75] Inventors: Louis L. Wood, Rockville; Gary J. Calton, Elkridge, both of Md.

[73] Assignee: Purification Engineering, Inc., Columbia, Md.

[*] Notice: The portion of the term of this patent subsequent to Mar. 13, 2001 has been disclaimed.

[21] Appl. No.: 765,962

[22] Filed: Aug. 15, 1985

Related U.S. Application Data

[63] Continuation of Ser. No. 518,756, Jul. 29, 1983, Pat. No. 4,600,692, which is a continuation-in-part of Ser. No. 465,551, Feb. 10, 1983, and a continuation-in-part of Ser. No. 358,784, Mar. 16, 1982, Pat. No. 4,436,813.

[51] Int. Cl.$^4$ ............... C12P 13/22; C12N 11/02; C12N 11/08; C12N 11/04

[52] U.S. Cl. .................... 435/108; 435/174; 435/177; 435/180; 435/182

[58] Field of Search ............ 435/108, 174, 177, 178, 435/180, 182

[56] References Cited

U.S. PATENT DOCUMENTS

| | | | |
|---|---|---|---|
| 4,304,858 | 12/1981 | Wandrey et al. | 435/106 X |
| 4,326,031 | 4/1982 | Wandrey et al. | 435/146 |
| 4,436,813 | 3/1984 | Wood et al. | 435/180 X |
| 4,450,233 | 5/1984 | Mimura et al. | 435/180 X |
| 4,452,892 | 6/1984 | Rosevear | 435/182 X |
| 4,518,692 | 5/1985 | Rozzell | 435/108 X |

FOREIGN PATENT DOCUMENTS

| | | | |
|---|---|---|---|
| 96388 | 8/1978 | Japan | 435/108 |
| 51991 | 5/1981 | Japan | 435/108 |

OTHER PUBLICATIONS

Yamada et al., Applied and Environmental Microbiology, vol. 42, No. 5, 1981, pp. 773–778.
Jack et al., Advances in Biochem. Eng. vol. 5, 1977 pp. 126–135.
Oishi, K., The Microbial Production of Amino Acids, John Wiley & Sons, N.Y., 1972, pp. 435–452.
Porath, et al., Methods in Enzymology, vol. XLIV, 1976, pp. 19–45.

*Primary Examiner*—David M. Naff
*Attorney, Agent, or Firm*—Cushman, Darby & Cushman

[57] ABSTRACT

Phenylalanine is produced by contacting cells having transaminase activity with phenylpyruvic acid or phenylpyruvate in the presence of an amine donor. The cells may be ruptured or permeabilized to release their transaminase activity. Preferably, the cells are immobilized with a polyazetidine polymer. Preferred reaction conditions are an excess of amine donor in a ratio of at least 1.1:1 amine donor to phenylpyruvic acid or phenylpyruvate and a pH of 5–10 such as to convert at least 85% of the phenylpyruvic acid or phenylpyruvate to phenylalanine. Phenylalanine may also be produced from cinnamic acid using immobilized cells having phenylalamine ammonia lyase activity.

7 Claims, No Drawings

PRODUCTION OF PHENYLALANINE WITH IMMOBILIZED CELLS

This is a continuation of application Ser. No. 518,756, filed July 29, 1983, now U.S. Pat. No. 4,600,692, which is a continuation-in-part of application Ser. No. 465,551, filed Feb. 10, 1983, and of application Ser. No. 358,784, filed Mar. 16, 1982, now U.S. Pat. No. 4,436,813. The disclosures of these earlier applications are incorporated herein by reference.

The present invention is primarily concerned with the production of phenylalanine from a precursor thereof, notably phenylpyruvate or phenylpyruvic acid, via transaminase. One embodiment of the invention utilizes immobilized whole cells having transaminase activity to produce phenylalanine from phenylpyruvate. However, according to a further embodiment of the invention, the desired enzyme activity may be obtained by using ruptured or permeabilized cells, as such or as purified fractions thereof, either in the free or immobilized state to obtain phenylalanine.

The invention also contemplates the possibility of preparing phenylalanine from cinnamic acid using immobilized whole cells having phenylalanine ammonia lyase activity.

The production of phenylalanine from phenylpyruvate has been attempted by numerous investigators. There are two possible routes to accomplish this transformation. One is by transamination with an appropriate amine donor while the other is direct reductive amination using a biological energy source such as NAD or NADP.

Sakurai (J. Biochemistry 43, 851, 1956) attempted the preparation of optically active amino acids via transamination. Sakurai used crude pig heart transaminase (freshly obtained) and found that after 20 hours the yield of phenylalanine reached a maximum of 78% when aspartic acid was used with a small amount of glutamic acid. When aspartic acid alone was used, the yield was only 70%. Sakurai concluded that both amino acids should be present for maximal yields. He explained this result as a coupled system in which glutamic acid was the amine donor for phenylalanine and the aspartic acid served to regenerate the glutamic acid.

Oishi ("The Microbial Production of Amino Acids", John Wiley & Sons, K. Yamada et al Eds. 1972, Chap. 16) reviewed the production of phenylalanine from precursor keto acids. He noted a maximum yield of 63.5% phenylalanine was obtained by Asai in screening a large number of microbes which had been dried. This yield was obtained from a strain of *Alcaligenes faecalis*. The two strains of *E. coli* surveyed showed a 38.5% and a 53% yield under the reaction conditions used. Asai obtained yields as high as 70.6% when the amine donor was a combination of L-aspartate, L-glutamate and L-leucine. Yields with aspartate in two-fold excess were only 54.5%.

It will be appreciated that the yields noted above with respect to the indicated prior procedures are not suitable for an economic industrial process. Yields in excess of 90% are generally considered essential for a commercially viable process.

Oishi also reported that, by using a coupled enzyme system, Kitai was able to reach 76.8% yield. The coupled system was a yeast alcohol dehydrogenase with beef liver glutamate dehydrogenase and the *Serratia marscescens* glutamate-phenylalanine amino transferase. The reaction was driven by the removal of acetaldehyde by semicarbazide. Additionally, Kitai was able to drive the reaction to the expected 100% yield of L-phenylalanine by use of a coupled system for reductive amination in which *E. coli* were used to provide NADP. Glutamate, which served as the amine donor, was the limiting reagent.

Wandrey et al (U.S. Pat. No. 4,304,858) describe a coupled system (with formate dehydrogenase) for the production of phenylalanine from phenylpyruvate while providing exogenous NAD or NADH. The system is also applicable when using alphahydroxycarboxylic acid for the precursor as illustrated in U.S. Pat. No. 4,326,031. In both of these systems, however, it is necessary to use the reagent NAD or NADH and to use a coupled system in order to regenerate this expensive and labile material.

The available literature reviewed above indicates that only when using coupled systems are high yields of phenylalanine obtained from phenylpyruvate. When uncoupled systems are used, yields no higher than 71% have been obtained using three different amine donors.

An important object of the invention is to provide a process for the production of phenylalanine in high yields from phenylpyruvic acid or phenylpyruvate via transaminase. A more specific object is to prepare phenylalanine by such a process which involves a single step, with a single amine donor and requiring neither a coupled system nor the addition of expensive cofactor reagents such as NADP or NAD. Other objects will also be hereinafter apparent.

According to the invention, phenylalanine is produced from phenylpyruvic acid or phenylpyruvate by transaminase using immobilized whole cells. In another embodiment of the invention, cells are used which have been ruptured or permeabilized so as to release their transaminase activity. These ruptured or permeabilized cells may be in the free or immobilized state.

In our above-mentioned earlier applications, we have described the preparation and use of compositions comprising whole cells having enzymatic activity wherein the cells are immobilized by means of an insoluble, crosslinked polymer obtained by curing a polyazetidine prepolymer, carboxymethyl cellulose, polyurethane hydrogel prepolymer or polymethylene isocyanate. Preferably the immobilizing polymer is a polyazetidine polymer although the other disclosed polymers may be used. Advantageously the immobilized cells are coated onto beads or other particulate material.

According to Ser. No. 465,551, cells may be immobilized using polyazetidine prepolymers which may be crosslinked in aqueous solution by reaction with =NH, —SH, —OH, —COOH; or other polyazetidines which may be crosslinked by H₂O removal, heat, or by changing to a more basic pH. The following is an idealized structure of a representative polyazetidine such as Polycup TM 172 (Hercules, Inc.) which is useful for present purposes:

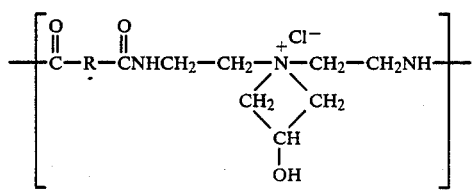

where R is typically —$CH_2)_4$.

The present invention contemplates the use of immobilized cell compositions as described in said earlier applications, as well as other forms of immobilized cells, provided the immobilized cells have transaminase activity. According to the invention, phenylalanine is produced by contacting a phenylalanine precursor, specifically phenylpyruvate or phenylpyruvic acid, with the immobilized cell composition having transaminase activity in the presence of an amine donor, so that the precursor is converted to phenylalanine. The literature indicates that small amounts of pyridoxal-5-phosphate (P5P) are required by the transaminase as a co-factor. This material (P5P) is also used in the present process in conventional co-factor amounts.

The precursor may be used in the form of the free acid or as a salt thereof, e.g. the ammonium or alkali metal salt.

A wide variety of amine donors may be used provided these are active with the transaminase. Preferably the donor is L-glutamic acid, L-aspartic acid or mixture thereof. However, other amine donors such as L-leucine or L-isoleucine may also give highly useful results. Preferably the donor is used in excess and it appears that higher yields are obtained as the excess is increased up to, for example, 30-50% excess or even more.

Any microorganism demonstrating transaminase activity may be used for present purposes. A wide variety of these are known (see Table 16-3, page 441, of Oishi publication mentioned above). These include the following:

Alcaligenes faecalis
Pseudomonas cruciviae
Pseudomonas aeruginosa MT
Aerobacter aerogenes
Escherichia coli
Achromobacter cycloclastes
Sarcina lutea
Kluyvera citrophila
Pseudomonas fluorescens
Micrococcus lysodeikticus.

The reaction conditions used for carrying out the transaminase reaction according to the invention can be widely varied, as will be understood by those in the art. For example, an aqueous solution of the precursor can be passed through a column containing the immobilized cells containing transaminase activity and the amine donor. Optimum ratios of precursor to donor and to cells, and other operating conditions, can be readily determined for any specific situation without undue experimentation. Typically, however, the ratio of the amine donor to the precursor will be at least 1:1 and preferably 1.1:1 or higher, e.g. 3:1. A preferred ratio is 1.5-2 parts donor per part precursor, parts being on an equivalent weight basis.

Acid or alkaline pHs may be used although there will generally be a readily determined optimum pH for any particular set of conditions. Usually it is desirable to use a pH above 4, and generally one in the range of 5-10, although pHs outside these ranges may also be used. Temperatures of 30° to 40° C. normally will be used although any temperature below transaminase deactivation can be used.

The invention is illustrated by the following examples:

EXAMPLE 1

Saccharomyces cervisiae, E. coli, Alcaligenes faecalis and Pseudomonas dachunae cells were immobilized in separate batches with polyazetidine as described in Ser. No. 465,551 (see, for instance, example 8 thereof) by mixing equal parts of cell paste and aqueous polyazetidine solution (Hercules Polycup 172), stirring to homogenity at 25° C. by hand mixing with a wooden stick. This mixture was dispersed on Amberlite ion exchange beads which had been air-dried. The thin film of paste/prepolymer mixture on the beads was allowed to air dry at 25° C. One ml of each group of beads containing 0.2 grams of microbial cells per ml of beads was then placed into a 50 ml Erlenmeyer flask containing 25 ml of a 0.1M aqueous solution of sodium pyruvate and either L-glutamic acid, L-aspartic acid or mixture thereof as amine donor and 0.1 mM of P5P. These were then compared with the use of free cells of Pseudomonas and Alcaligenes under otherwise similar conditions. The results in terms of phenylalanine (PHE) produced were determined by HPLC analysis of the supernatant after 17 hours of shaking and are presented below in Table I.

TABLE I

Transamination of Phenylpyruvic Acid (PPA) To Yield Phenylalanine (PHE)

| Microbe | Concentration PHE Formed Amine Donor: | | |
|---|---|---|---|
| | ASP & GLU | GLU | ASP |
| Saccharomyces cerevisiae | — | .012 M | <.002 M |
| E. coli | .024 M | .027 M | .013 M |
| A. faecalis | .01 M | .014 M | <.002 M |
| P. dacunhae | .024 M | .028 M | <.002 M |

(The references to "ASP" and "GLU" above represent L-aspartic acid and L-glutamic acid, respectively.)

The foregoing example demonstrates that whole cells immobilized as described and having transaminase activity may be effectively used to produce phenylalanine from phenylpyruvate precursor when an appropriate amine donor is employed.

In the control using Pseudomonas and Alcaligenes in the fresh, wet free state (unruptured and unpermeabilized), negligible transaminase activity was noted. However, on rupturing the cells or by permeabilizing them, activity was substantially increased. This is surprising because the literature indicates that dried cells, which would normally be considered lysed or permeabilized, do not give commercially acceptable conversions.

Accordingly, the use of ruptured or permeabilized cells, whether immobilized or in the free state, to prepare phenylalanine constitutes a further aspect of the invention. Various techniques may be used to rupture or permeabilize the cells for use according to the invention. For example, the cells may be ruptured by sonication or grinding as known in the art. Alternatively the cells may be permeabilized by chemical treatment, e.g. by treatment with a permeabilizing surfactant such as Triton X100. These treatments apparently allow the phenylpyruvate or phenylpyruvic acid to more readily contact the enzyme and thus improve activity whether or not the microorganism is immobilized.

The use of ruptured cells, and the effect of pH and amine donor level on the results, are described in the following example:

EXAMPLE 2

2 grams of free E. coli cells were sonicated for 10 minutes in order to rupture the cells after which they were incubated for 23 hours with 25 ml aqueous solution containing different amounts of ASP (0.10M, 0.15M and 0.2M), 0.1 mM P5P and 0.1M PPA at 37° C. on a Dubnoff H$_2$O shaker. H$_3$PO$_4$ was used for pH adjustment.

The results obtained are shown below in Table II.

TABLE II

| ASP Level: | .10 M | .15 M | .2 M |
|---|---|---|---|
| pH | % Conversion (PPA to PHE) | | |
| 7 | — | 87 | — |
| 8.4 | 77.6 | 90 | 96.7 |

As shown, free cells, when ruptured, give the best and most useful conversions at higher ASP concentrations, the data given in Table II indicating that for a commercially acceptable yield level, the amount of ASP should exceed the amount of substrate on a molar equivalence basis.

The various aspects of the invention are further illustrated by the following additional examples:

EXAMPLE 3

Table III shows the effect of pH on transaminase activity using E. coli whole cells immobilized in bead form as in Example 1. Three experiments were conducted using 2 ml of beads incubated in 15 ml of 0.1M PPA, 0.1 mM P5P and 0.15M ASP at 37° C. for 24 hours. The pH was adjusted with 1N NaOH or 1N HCl.

TABLE III

| Experiment 1 Immobilized Cells 24 hours | | Experiment 2 Immobilized Cells 4 hours | | Experiment 3 Free Cells 4 hours | |
|---|---|---|---|---|---|
| pH | % Conv. | pH | Activity (units)* | pH | Activity (units) |
| 5.0 | 95.9 | 3 | 32 | 3 | 78 |
| 5.5 | 96.5 | 4 | 99 | 4 | 94 |
| 6.0 | 95.0 | 5 | 219 | 5 | 123 |
| 6.5 | 95.9 | 6 | 212 | 6 | 601 |
| 7.0 | 95.1 | 7 | 217 | 7 | 598 |
| 8.0 | 94.7 | 8 | 207 | 8 | 571 |
| | | 9 | 209 | 8.4 | 586 |
| | | 10 | 156 | 9 | 637 |
| | | | | 10 | 115 |

*A unit is 1 micromol per hour per gram of wet cells.

The data in Table III shows that high yields of PHE similar to those obtainable with ruptured free cells can be obtained using immobilized E. coli.

EXAMPLE 4

Table IV below provides the results in terms of yield of PHE obtained using immobilized E. coli in a continuous column operation (300 ml, 3.5×70 cm) with 0.1M PPA, 0.15M ASP and 0.1 mM P5P.

TABLE IV

| | Experiment 1 | Experiment 2 |
|---|---|---|
| DAY 1 | 95.1 | 100 |
| 8 | 91.2 | |
| 9 | 87.9* | |
| 10 | 92.1 | |
| 11 | 92.1 | 92 |
| 12 | 94.2 | |
| 13 | 95.1 | |
| 14 | 96.1 | |
| 15 | 94.8 | |
| 16 | 96.8 | |
| 17 | 95.8 | 85* |
| 18 | 95.3 | |
| 35 | | 91 |
| 42 | | 93 |
| 43 | | 97 |
| 45 | | 100 |

*It should be noted that occasional fluctuations in flow rates may show a reduced activity or yield on such occasions. However, the important factor is the maximum yield which is shown as this is indicative of the full potential of the process exemplified.

EXAMPLE 5

While polyazetidine polymer is preferred for immobilizing the microorganisms for use herein, the invention contemplates the possibility of using any other suitable immobilizing substrate. As representative of such alternatives, there may be mentioned such materials as polyacrylamide, Kappa-carrageenan, hollow fiber devices, Hypol or XAD coated beads. These materials have been shown to give excellent yields although the activity of the immobilized cells may vary from one immobilizing substrate to another. The results obtained in terms of yields and activities, using different systems involving immobilized E. coli, are shown below in Table V. The process used involved continuous flow onto a column of immobilized cells as described of an aqueous solution of 0.1M PPA, 0.15M ASP and 0.1 mM P5P at a pH 8.3–8.5 (adjusted with NH$_4$OH) at 37° C. Flow varied according to column activity and space occupied. Equilibrium was reached at optimal flow prior to taking readings.

TABLE V

| Cell Immobilization Method | Max. Yield Observed | Activity (Units)* |
|---|---|---|
| E. coli coated on XAD beads with Polycup | 91 | 34 |
| E. coli coated on IRA938 beads with Polycup | 98 | 63 |
| E. coli with HYPOL foam | 95 | 53 |
| E. coli with Kappa-carrageenan gum | 100 | 29 |
| E. coli in a hollow fiber device | 91 | 82 |

*1 unit of activity is defined as 1 μmole/hr/g cells (wet wt.) at maximum conversion.

Of the materials referred to in Table V, XAD is a macroreticular styrene-divinylbenzene resin; IRA 938 is an ion exchange bead resin comprising styrene-divinylbenzene containing tertiary amine substituents; and Hypol is a polyurethane foam. The Kappa-carrageenan gum was cut into particles before use. The hollow fiber device was a commercially available item.

As an alternative to the procedures described above, phenylalanine may be made from cinnamic acid by using immobilized whole cells which are high in phenylalanine ammonia-lyase activity. This aspect of the invention represents an improvement in the process described by Yamada et al, Applied and Environmental Microbiology November 1981, pages 773–778, incorporated herein by reference.

Yamada et al describe the preparation of L-phenylalanine from trans-cinnamic acid by an enzymatic method using Rhodotorula glutinis containing L-phenylalanine ammonia-lyase activity. According to the present invention, Rhodotorula glutinis ATCC 10788 was grown as described by Yamada et al and the harvested cells were immobilized with polyazetidine prepolymer. 14.9 grams of cells were mixed with 14.9 grams of polyazetidine prepolymer and coated onto 13.8 grams of IRA 938 ion exchange resin and assayed for phenylalanine ammonia lyase activity. Cinnamic acid was added to the beads by mixing 1 ml of beads produced as above with 5 ml of assay mixture which contained 740 mg transcinnamic acid, 45 ml 28% ammonium hydroxide, pH 10 diluted to 80 ml. After 24 hours the supernatant was spotted on a cellulose TLC plate and developed in a mixture of butanol, acetic acid, water (4:1:1) and the plates were sprayed with 0.2% ninhydrin and ethanol. Standards of phenylalanine were used for comparison and an estimation based on intensity and size of the spot indicated that 0.05 mg/ml of phenylalanine had been produced.

It will be appreciated that various modifications may be made in the invention described herein.

Accordingly, the scope of the invention is defined in the following claims wherein:

We claim:

1. A process for preparing phenylalanine which comprises contacting phenylpyruvic acid or phenylpyruvate with cells having transaminase activity immobilized with a polyazetidine polymer in the presence of an excess of an amine donor in a ratio of at least 1.1:1 amine donor to phenylpyruvic acid or phenylpyruvate and at a pH of 5-10, said process being such as to convert at least 85% of the phenylpyruvic acid or phenylpyruvate to phenylalanine.

2. The process of claim 1 wherein the immobilized cells are coated onto beads or other particulate material.

3. The process of claim 1 wherein the excess of amine donor is at least 50%.

4. The proces of claim 1 wherein the donor is L-aspartic acid, L-glutamic acid or mixture thereof.

5. The process of claim 1 including pyridoxal-5-phosphate.

6. The process of claim 1 wherein the cells are *E. coli* cells.

7. The process of claim 1 wherein the cells are selected from the group consisting of
Pseudomonas dacunhae
Saccharomyces cerevisiae
Alcaligenes faecalis
Pseudomonas cruciviae
Pseudomonas aeruginosa MT
Aerobacter aerogenes
Escherichia coli
Achromobacter cycloclastes
Sarcina lutea
Kluyvera citrophila
Pseudomonas fluorescens
Micrococcus lysodeikticus.

* * * * *